United States Patent
Rey et al.

(10) Patent No.: US 10,180,391 B2
(45) Date of Patent: Jan. 15, 2019

(54) DEVICES AND METHODS FOR CONDUCTING ACCELERATED AGING TESTS OF A COATING WITH SEVERAL TYPES OF STRESSES

(71) Applicant: AIRBUS OPERATIONS (S.A.S.), Toulouse (FR)

(72) Inventors: Stéphane Rey, Lavernose Lacasse (FR); Florent Audoin, Toulouse (FR); Pierre Heberle, Plaisance du Touch (FR); Isabelle Multan, Mondonville (FR)

(73) Assignee: Airbus Operations (S.A.S.), Toulouse (FR)

( * ) Notice: Subject to any disclaimer, the term of this patent is extended or adjusted under 35 U.S.C. 154(b) by 421 days.

(21) Appl. No.: 14/977,963

(22) Filed: Dec. 22, 2015

(65) Prior Publication Data
US 2016/0187247 A1    Jun. 30, 2016

(30) Foreign Application Priority Data

Dec. 26, 2014   (FR) ...................................... 14 63352

(51) Int. Cl.
*G01N 17/00*      (2006.01)
*G01N 3/60*       (2006.01)
(Continued)

(52) U.S. Cl.
CPC ........ *G01N 17/002* (2013.01); *G01M 5/0091* (2013.01); *G01M 99/002* (2013.01); *G01N 25/00* (2013.01); *G01N 25/72* (2013.01)

(58) Field of Classification Search
USPC ....................... 374/57, 5, 142, 208
See application file for complete search history.

(56) References Cited

U.S. PATENT DOCUMENTS 5,767,423 A * 6/1998 Camp ................. G01N 17/004
374/57
6,113,262 A     9/2000 Purola et al.
(Continued)

FOREIGN PATENT DOCUMENTS

JP         3 077 597 B2    8/2000
WO    WO 2014/118200 A1   8/2014

OTHER PUBLICATIONS

Bib Data for JP 3077597 (Aug. 14, 2000).*
(Continued)

*Primary Examiner* — Mirellys Jagan
(74) *Attorney, Agent, or Firm* — Jenkins, Wilson, Taylor & Hunt, P.A.

(57) ABSTRACT

A device for conducting accelerated aging tests of a coating, notably an outer coating for an aircraft, in particular allowing the testing of the durability of the coating after having been subject to all kinds of stresses, is desired. An object of the disclosure thus relates to such a device including test chambers subject to different and/or independently controllable test parameters, and including light for generating photo-oxidation, the device including a support for a sample of the coating, displaceable between the chambers for generating mechanical stresses by thermal shocks. The disclosure herein finds applications in many fields of industry, and preferentially in the field of aeronautics.

16 Claims, 2 Drawing Sheets

(51) Int. Cl.
  *G01K 1/00* (2006.01)
  *G01N 25/00* (2006.01)
  *G01N 25/72* (2006.01)
  *G01M 99/00* (2011.01)
  *G01M 5/00* (2006.01)

(56) References Cited

U.S. PATENT DOCUMENTS

| | | | | |
|---|---|---|---|---|
| 6,271,024 | B1* | 8/2001 | Sve | G01N 3/60 |
| | | | | 165/254 |
| 6,360,621 | B1* | 3/2002 | Eldred | G01M 99/002 |
| | | | | 73/865.6 |
| 6,367,340 | B1 | 4/2002 | Hayes et al. | |
| 7,038,196 | B2* | 5/2006 | Scott | G01N 17/002 |
| | | | | 250/252.1 |
| 7,348,581 | B2* | 3/2008 | March | G01N 17/004 |
| | | | | 250/504 R |
| 2014/0153609 | A1* | 6/2014 | Jing | G02F 1/1309 |
| | | | | 374/57 |

OTHER PUBLICATIONS

Translation of JP 3077597 (Aug. 14, 2000).*
French Search Report for Application No. 14 63352 dated Jul. 16, 2015.

* cited by examiner

DEVICES AND METHODS FOR CONDUCTING ACCELERATED AGING TESTS OF A COATING WITH SEVERAL TYPES OF STRESSES

CROSS-REFERENCE TO RELATED APPLICATION

This application claims priority to French Patent Application FR 14 63352 filed Dec. 26, 2014, the entire disclosure of which is incorporated by reference herein.

TECHNICAL FIELD

The present disclosure relates to the field of devices which are designed for conducting accelerated aging tests of a coating, and in particular an outer coating for an aircraft, this accelerated aging being representative of the aging in service of the coating.

More specifically, the disclosure herein thus proposes devices and methods for conducting accelerated aging tests of a coating, as well as an associated method.

Its application is mainly in the field of aeronautics, in particular for characterization of the durability of the outer coatings applied on aircraft.

BACKGROUND

For purposes of illustration of the technical context of the disclosure herein, FIG. 1 shows in a view from above an example of an aircraft 10, the fuselage 11 of which comprises an outer coating R.

Habitually, the outer coatings used in aircraft, for example a coating R of the type used for the fuselage 11 of the aircraft 10 represented in FIG. 1, undergo degradations in service. These can be grouped into two main categories, i.e. degradations caused by optical deterioration and degradations caused by mechanical deterioration.

In the case of optical deterioration, the degradations correspond to faults associated with a change such as the brightness or color of the coating. For example, this can involve yellowing and/or a loss of brightness of the coating, inter alia.

In the case of mechanical deterioration, the degradations correspond to physical defects of the coating. For example, this can involve cracking and/or detachment, inter alia.

The origin of these degradations of the coating can be explained by the combination of several stresses, in particular associated with photo-oxidation, temperature and humidity, and the mechanical aspect. The photo-oxidation corresponds to the chemical aging of the coating when it is subjected to solar radiation. The stresses caused by temperature and humidity are derived from a substantial and rapid variation of temperature and humidity. Finally, the mechanical stresses correspond to the stresses induced by the structure of the aircraft, to which the coating is subjected.

In order to study the degradations of the coating of an aircraft during its service life, tests are conventionally carried out, in particular in order to characterize the durability of the coating. However, the tests which are performed habitually are often lengthy, and take into account only a single parameter, typically the temperature, humidity, or also ultraviolet radiation. However, an approach of this type is not representative of the behavior in service of the outer coating, and does not make it possible to track down the degradations observed on the coating.

In addition, the prior art does not teach a solution for carrying out accelerated aging tests of a coating taking into account the combination or succession of stresses which give rise to the degradations (photo-oxidation, variation of temperature and humidity, mechanical stresses, etc.) to which it is subjected, for the purpose of reproducing these degradations.

In reality, at present, there are firstly enclosures which make it possible to carry out photo-oxidation on a coating sample for an aircraft in order to test its durability in accelerated aging conditions.

FIG. 2 illustrates in cross section an example of an enclosure 12 for accelerated photo-aging according to the prior art, in order to carry out photo-oxidation on a coating sample R of an aircraft.

In this enclosure 12, test pieces 13 for sampling of the coating R are secured on a test piece support 14, and subjected to exposure to a xenon lamp 15 situated inside the support 14, as represented in FIG. 2. The temperature of the enclosure 12 is for example approximately 55° C., in order to permit exposure of the test pieces 13 to the photo-oxidation, and carry out the tests of durability of the coating R after accelerated aging.

In addition, there are also enclosures which make it possible to apply mechanical stresses by thermal shocks on a coating sample for an aircraft, in order to test its durability in accelerated aging conditions.

FIG. 3 illustrates in cross section an example of an enclosure 12 for accelerated aging by thermal shocks according to the prior art, in order to apply mechanical stresses on a coating sample R of an aircraft.

In this type of enclosure 12, two sub-enclosures 12a and 12b are provided, placed on top of one another and separated by a wall 16 which is provided with an opening 16a. In addition, a support 14 for sampling test pieces of the coating R is provided in the enclosure 12. This support 14 can be displaced vertically according to the double arrow F between the sub-enclosures 12a and 12b, in order to subject sampling test pieces to thermal shocks. The displacement of the support 14 then makes it possible to close the opening 16a in the wall 16 by one of its flanks, as in the case of its positioning represented in broken lines in FIG. 3 within the sub-enclosure 12b.

In order to be able to test pieces which are situated in the support 14 to thermal shocks, the temperature T1 of the sub-enclosure 12a is clearly distinct from the temperature T2 of the sub-enclosure 12b. In particular, the temperature T1 can be selected as approximately 70° C., whereas the temperature T2 can be selected as approximately −55° C. This considerable difference between the temperatures T1 and T2 makes it possible to obtain a thermal shock during the passage of the support 14 from one sub-enclosure to the other.

Thus, for example it is possible to create a thermal shock which gives rise to mechanical stresses on the sampling test pieces of the coating R, by placing the support 14 in the sub-enclosure 12a with the temperature T1 of approximately 70° C., with the lower flank of the support 14 closing the opening 16a in the wall 16. Then, the support 14 is displaced vertically towards the sub-enclosure 12b by any type of mechanism, for example such as, inter alia, by an articulated arm or by a jack which thrusts the support 14 upwards or downwards, which sub-enclosure is at a temperature T2 of approximately −55° C., the opening 16a in the wall 16 then being closed by the upper flank of the support 14, and the sampling test pieces of the coating R being subjected to thermal shock of the rapid passage from T1 to T2.

However, these two types of enclosures previously described are not entirely satisfactory for carrying out accelerated aging tests of outer coatings of an aircraft which are sufficiently representative of the real wear sustained in service by these coatings. In particular, the prior art does not teach a solution which makes it possible to combine at least these two types of stresses (photo-oxidation and mechanical stresses by thermal shocks) even though this combination of stresses is representative of the real aging observed in service.

SUMMARY

There is thus a need to design a new type of device in order to conduct accelerated aging tests of a coating, in particular an outer coating for an aircraft, in order to test the durability of the coating after it has been subjected to all kinds of stresses. In particular, there is a need to provide a device of this type which can make it possible to generate stresses of different types on the coating to be tested.

An objective of the disclosure herein is partially at least to fulfill the aforementioned needs, and eliminate the disadvantages relating to the embodiments of the prior art.

According to one of its aspects, the subject of the disclosure herein is thus a device for conducting accelerated aging tests (also known as an accelerated aging device) of a coating, in particular an outer coating for an aircraft, wherein it comprises at least a first test chamber and a second test chamber which are separated by a mobile partition, each chamber being subjected to accelerated aging test parameters, comprising at least the temperature and the level of humidity, the test parameters being different from one chamber to the other and/or controllable independently from one chamber to the other, each chamber additionally comprising a light in order to generate photo-oxidation, and wherein the device also comprises a support for retention of at least one sample of the coating, the support being displaceable from the first chamber to the second chamber and conversely, after opening of the mobile partition between the first and second chambers in order to generate mechanical stresses by thermal shocks.

By the disclosure herein, it can be possible to produce a device for conducting accelerated aging tests of coatings, which makes it possible to obtain tests which are more representative of the behavior in service of the coatings, in particular of the decorative outer coatings, and thus to guarantee the durability of the coatings. The device according to the disclosure herein thus makes it possible to approximate as well as possible the real circumstances of the coating. In fact, in the case of an outer coating for an aircraft on the ground, the aircraft is subjected to temperatures which vary between approximately −20° C. and 50° C., and also to exposure to light. In flight, the aircraft is subjected to temperatures of approximately −55° C., and also to exposure to light. Thus, the aircraft goes from one environment to the other, in particular at takeoff and/or landing. The device according to the disclosure herein can make it possible to reproduce this environment of the aircraft in order to conduct accelerated aging tests.

The device according to the disclosure herein can also comprise one or more of the following characteristics taken in isolation or according to any technically possible combinations.

The partition which is mobile between the first and second chambers is advantageously solid, in other words without an opening. The absence of an opening in the mobile partition can make it possible to obtain better temperature sealing between the first and second chambers, as well as a saving in consumption. In fact, in this case, no support flank is subjected to a different temperature.

At least one of the light, and in particular each light, can be fitted in translation along an axis, such as to be able to be displaced to and from the at least one sample of the outer coating situated in the support.

An axis of this type can for example be a central axis, or any other type of axis, which in particular is vertical or not vertical.

However, the displacement in translation of each light along its associated axis is advantageously a displacement according to a direction perpendicular to the direction of displacement of the support between the first and second chambers, in particular a displacement which is vertical relative to the horizontal plane on which the device is placed.

Each light advantageously comprises a lamp, in particular a lamp of the xenon or mercury type.

The operating system, and in particular the system for displacement of one of the light, is also advantageously independent from the other one of the light. In other words, the light are advantageously controllable independently from one another.

The operating system of each light preferably comprises a motor in order to permit the displacement of the light.

The support advantageously comprises an opening, in particular an upper opening, in order to permit the passage of each light, i.e. the displacement of each light from the interior to the exterior of the support, and conversely.

In addition, the device can comprise at least one compartment outside the first and second chambers, in particular a first compartment outside the first chamber and a second compartment outside the second chamber, in which at least one of the light can be accommodated in the case when the light is not used. In particular, the device can comprise a first compartment outside the first chamber and a second compartment outside the second chamber, the first light of the first chamber being able to be accommodated in the first outside compartment in the case when the first light is not used, and the second light of the second chamber being able to be accommodated in the second outside compartment in the case when the second light is not used.

In addition, the temperature ranges which are possible in the first and second chambers are advantageously different, and selected so as to generate thermal shocks at the passage between the two chambers, the temperature range possible for one of the chambers being in particular between 0 and 250° C., and the temperature range possible for the other one of the chambers being in particular between −70 and 250° C.

The range of levels of humidity which is possible in the first and second chambers can be identical for the two chambers, and in particular can be between 0 and 100%. Advantageously, the ranges of levels of humidity of the first and second chambers can be controlled independently from one another in each chamber.

The walls of the mobile partition and/or the walls of the first and second chambers can preferably be thermally insulated in order to permit simultaneous operation of the two chambers at different temperatures.

In addition, at least one of the first and second chambers can comprise a system for spraying liquid inside the support.

Also, the support can comprise a first support part and a second support part, the first support part permitting retention of the at least one sample of the coating, and being fitted such as to rotate relative to the second support part.

The second support part can additionally comprise elements for displacement of the support, in particular notched wheels which cooperate with a displacement rail, in particular a notched rail of the device, which extends continuously between the two, first and second chambers.

The displacement of the support between the first and second chambers can make it possible to avoid handling of the support in an environment at ambient temperature, which would prevent thermal shocks. In reality, the time of passage from one chamber to the other and the time which the support takes to adopt the new temperature of the chamber to which it has been displaced are equivalent to the take-off and/or landing time.

In addition, according to another one of its aspects, the subject of the disclosure herein is also a method for conducting accelerated aging tests of a coating, in particular an outer coating for an aircraft, wherein it is implemented by a device as previously defined, and wherein it comprises carrying out once or more a step i) of optical stresses by photo-oxidation and/or a step ii) of mechanical stresses by thermal shocks, as described hereinafter:

i) submission of at least one sample of the coating, retained by the support situated in the first chamber or in the second chamber, which is closed by the mobile partition, to exposure to light of a first light of the first chamber, or respectively of a second light of the second chamber;

ii) submission of at least one sample of the coating, retained by the support situated in the first chamber or in the second chamber, which is closed by the mobile partition, to first accelerated aging test parameters comprising at least a first temperature and a first level of humidity, or respectively to second accelerated aging test parameters comprising at least a second temperature and a second level of humidity; then opening of the mobile partition in order to permit the displacement of the support from the first chamber to the second chamber, or respectively from the second chamber to the first chamber, and closure of the mobile partition when the support is situated in the second chamber, or respectively in the first chamber; and submission of the second chamber to second accelerated aging test parameters comprising at least a second temperature and a second level of humidity, or respectively submission of the first chamber to first accelerated aging test parameters comprising at least a first temperature and a first level of humidity, at least the first and second temperatures being different, such as to generate thermal shocks, the temperature difference between the first and second temperatures being equal to, or more than, 100° C., preferably 120° C., and even more preferably 130° C.

In addition, the method can comprise the implementation in succession of at least one step i) of optical stresses by photo-oxidation, then at least one step ii) of mechanical stresses by thermal shocks, or conversely.

Also, if applicable, during at least one step i) of optical stresses by photo-oxidation, the method can comprise spraying of a liquid into the first chamber or into the second chamber by a first liquid spraying system, or respectively by the second liquid spraying system, in particular during rotation of a first support part relative to a second support part of the support.

Moreover, if applicable, during at least one step ii) of mechanical stresses by thermal shocks, the method can comprise submission of the at least one sample of the coating, retained by the support situated in the first chamber or in the second chamber, which is closed by the mobile partition, to exposure to light of a first light of the first chamber, or respectively of a second light of the second chamber.

The method can also comprise repetition, according to a number n equal to 2 or more, of all the steps previously described of an accelerated aging cycle, such that the method comprises as many accelerated aging cycles as necessary for the definition given of the accelerated aging tests of the coating.

The device and the method according to the disclosure herein can comprise any one of the characteristics previously described, taken in isolation or according to any combinations which are technically possible with other characteristics.

BRIEF DESCRIPTION OF THE DRAWINGS

The disclosure herein will be able to be better understood by reading the following detailed description of a non-limiting embodiment of it, as well as by examining the schematic and partial figures of the appended drawing, in which.

In all of these figures, identical references can designate elements which are identical or similar.

In addition, the different parts represented in the figures are not necessarily according to a regular scale, in order to make the figures more legible.

DETAILED DESCRIPTION

Figure 1:
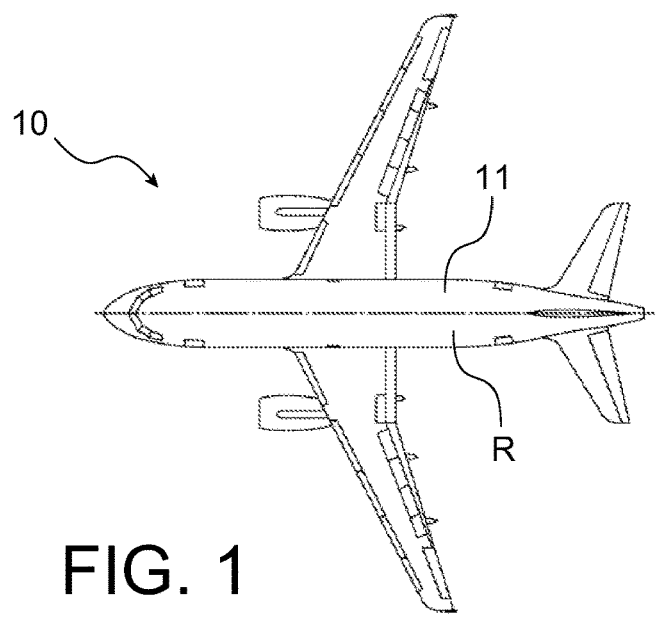
FIG. 1 represents in a view from above an example of an aircraft, the fuselage of which comprises an outer coating.
Figure 2:
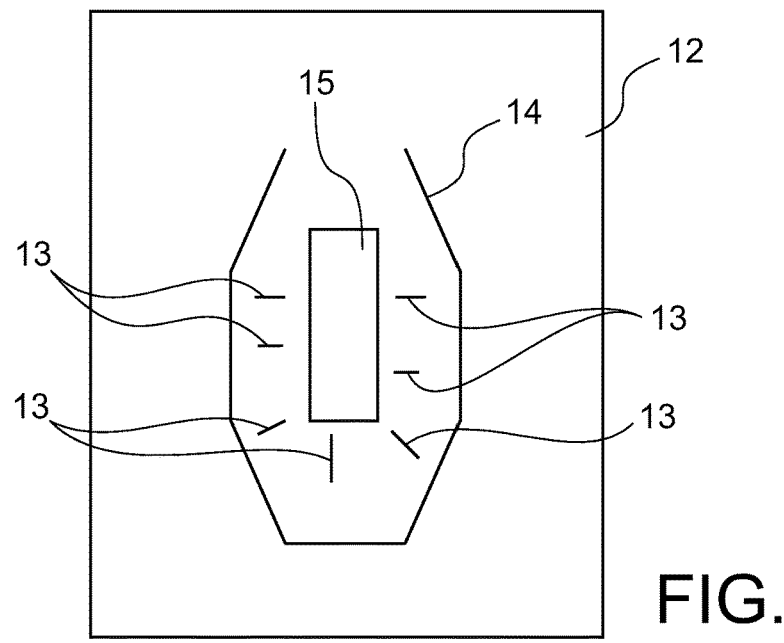
FIG. 2 illustrates in cross section an example of an enclosure for accelerated photo-aging by photo-oxidation according to the prior art, for the creation of optical stresses on a sample of aircraft coating.
Figure 3:
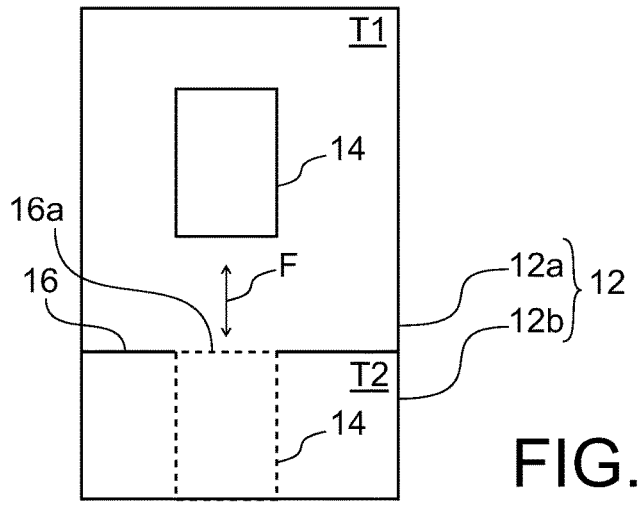
FIG. 3 illustrates in cross section an example of an enclosure for accelerated aging by thermal shocks according to the prior art, for the creation of mechanical stresses on a sample of aircraft coating.

A description is provided hereinafter of an embodiment of the disclosure herein with reference to FIG. 4. FIGS. 1 to 3, relative to the technical context of the disclosure herein and to the prior art, have previously been described.

Figure 4:
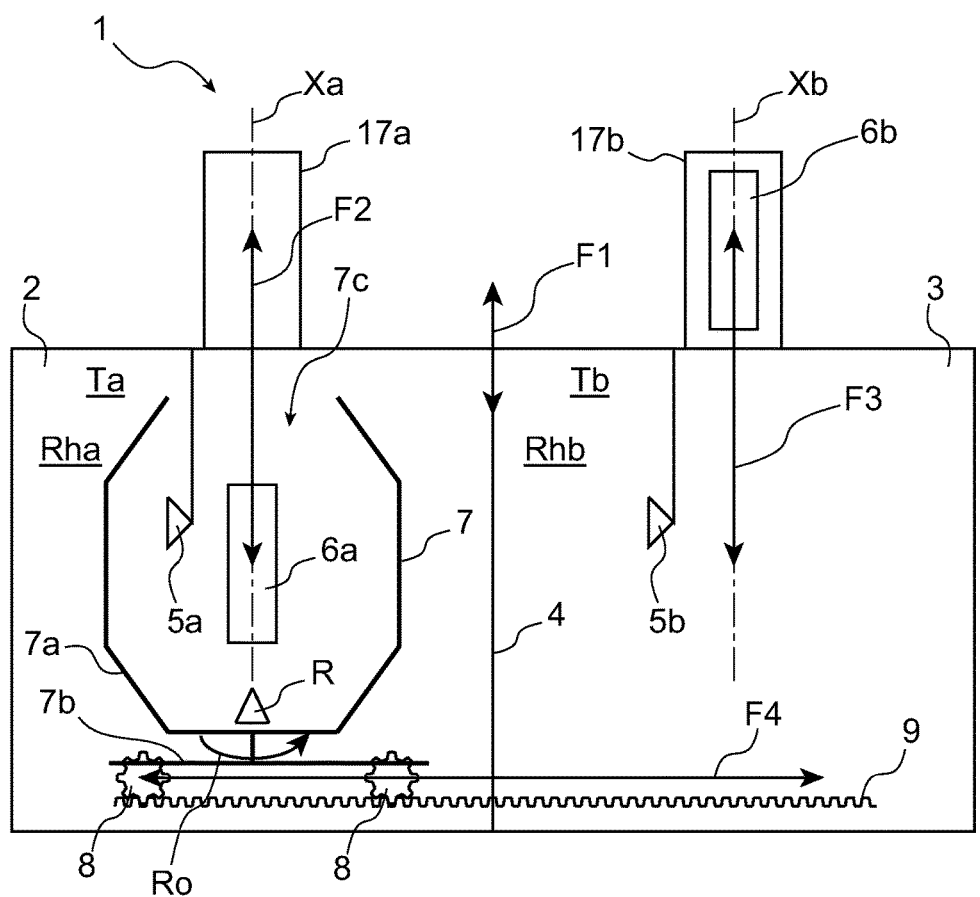
FIG. 4 illustrates in cross section an embodiment of a device according to the disclosure herein, for conducting accelerated aging tests of an outer coating for an aircraft.

FIG. 4 illustrates in cross section an embodiment of a device 1 according to the disclosure herein for conduction of accelerated aging tests of an outer coating R for an aircraft.

The device 1 is in the form of a test bench comprising a first test chamber 2 and a second test chamber 3 separated by a mobile partition 4, which can be displaced vertically according to the double arrow F1.

The two chambers 2 and 3 can be similar in terms of dimensions. Each of the chambers 2, 3 is subjected to accelerated aging test parameters which are determined according to the implementation conditions selected for the tests. These parameters are different for the two chambers 2, 3, and can be controlled independently during the tests.

In addition, these parameters comprise both the temperature $T_a$, $T_b$ and the level of humidity $Rh_a$, $Rh_b$ of the two chambers 2, 3. More specifically, the first chamber 2 is subjected to a first, high temperature $T_a$ of between 0 and 250°, and in particular approximately 60° C. In parallel, the second chamber 3 is subjected to a second, low-temperature $T_b$ of between −70 and 250° C., and in particular approximately −70° C. The significant difference in temperature between the first 2 and second 3 chambers has the objective of being able to create mechanical stresses by thermal shocks.

In addition, the conditions of hygrometry in each of the two chambers 2, 3 are such that the first chamber 2 is subjected to a level of humidity Rha, and the second chamber 3 is subjected to a level of humidity Rhb, which are between 0 and 100%.

In addition, in order to ensure correct operation of the two chambers 2, 3 at different temperatures, the walls of the mobile partition 4 and the walls of the first 2 and second 3 chambers are insulated thermally.

Also, as can be seen in FIG. 4, each chamber 2, 3 comprises a light 6a, 6b in order to generate photo-oxidation on the outer coating sample R.

The first 6a and second 6b light of the first 2 and second 3 chambers are in particular constituted by lamps, in particular of the xenon or mercury type.

These first 6a and second 6b light operate independently, and are in particular controlled independently in their displacements.

As can be seen in FIG. 4, the first lamp 6a is fitted in translation along a first central axis Xa, in order to permit its vertical displacement from the top downwards and from the bottom upwards, according to the double arrow F2. By this structure, the first lamp 6a can be displaced to and from the sample of the coating R. Also, the second lamp 6b is fitted in translation along a second central axis Xb, in order to permit its vertical displacement from the top downwards and from the bottom upwards, according to the double arrow F3. By this structure, the second lamp 6b can be displaced to and from the sample of the coating R.

In order to ensure the vertical displacements of the first 6a and second 6b lamps, the lamps are associated with a motorized operating system.

In addition, the device 1 comprises a first compartment 17a outside the first chamber 2, and a second compartment 17b outside the second chamber 3. These two compartments 17a and 17b are situated respectively on the upper surfaces of the first 2 and second 3 chambers.

These two compartments 17a and 17b have a size smaller than that of the first 2 and second 3 chambers. The two compartments 17a and 17b are each for example in the form of a rectangular tube. They are respectively in connection with the first 2 and second 3 chambers by their opening, respectively towards the upper surfaces of the first 2 and second 3 chambers. However, the two compartments 17a and 17b make it possible to close respectively the first 2 and second 3 chambers in a sealed manner.

When the first compartment 17a or the second compartment 17b communicates with the first chamber 2 or respectively the second chamber 3, by its opening, the first compartment 17a and the first chamber 2, and respectively the second compartment 17b and the second chamber 3, form one and the same enclosure.

The presence of the first 17a and second 17b compartments makes it possible to bring the first 6a and second 6b lamps as close as possible to the coating R inside the support 7 described hereinafter.

Thus, the first lamp 6a of the first chamber 2 can be accommodated in the first outside compartment 17a if the latter is not used. Similarly, the second lamp 6b of the second chamber 3 can be accommodated in the second outside compartment 17b if the latter is not used.

In addition, in order to ensure the displacement of the first 6a and second 6b lamps from their respective compartment 17a, 17b to the coating sample R, the support 7 of the coating sample R described hereinafter comprises an upper opening 7c which permits the passage of each lamp 6a, 6b.

In fact, in order to arrange the coating sample R which is designed to undergo the accelerated aging so as to determine its durability under the effect of a plurality of stresses, the device 1 comprises a support 7 for retention of this sample, which for example can be assimilated to a carousel.

This support 7 can be displaced from the first chamber 2 to the second chamber 3 and conversely, when the mobile partition is displaced upwards according to the arrow F1. By this structure, the passage of the support 7 from the first chamber 2 to the second chamber 3 generates mechanical stresses by thermal shocks.

As can be seen in FIG. 4, the support 7 comprises a first support part 7a and a second support part 7b. The first support part 7a makes it possible to retain the coating sample R. It is also fitted such as to rotate according to the arrow Ro relative to the second support part 7b.

The first support part 7a is for example in the form of a hollow enclosure provided with a single opening corresponding to the upper opening 7c of the support 7. This first support part 7a can comprise a plurality of inner walls, a lower inner wall of which, which is preferably substantially horizontal, makes it possible to receive the coating sample R. These inner walls can also have any type of form.

In addition, the second support part 7b comprises elements 8 for displacement of the support 7 in the form of notched wheels 8 which cooperate with a notched displacement rail 9 of the device 1. This notched rail 9 can extend between the first 2 and second 3 chambers.

In addition, the first 2 and second 3 chambers also each comprise a system 5a, 5b for spraying liquid inside the support 7, for example water or any other liquid. The spraying of this liquid can be programmed.

Finally, the device 1 comprises sensors, in particular thermal and/or hygrometry sensors, in order to regulate accelerated aging test parameters of the first 2 and second 3 chambers, in particular such as those described hereinafter.

A description will now be provided of the steps of a method for conducting accelerated aging tests of a coating R for an aircraft 10, implemented by the device 1 previously described with reference to FIG. 4. In particular, the steps of an aging cycle are described hereinafter. It will be appreciated that an aging cycle of this type can be repeated n times according to the definition of the tests to be carried out on the coating R. In addition, this repetition of the aging cycle will make it possible to reproduce the aging in service of the outer coating R with greater precision. Furthermore, the order of the steps described hereinafter can be inverted if applicable.

Firstly, the method comprises the step i) of creating optical stresses by photo-oxidation.

For this purpose, the coating sample R is placed on the support 7 situated inside the first chamber 2, which is closed by the mobile partition 4. The first lamp 6a is a lump of the xenon or mercury type, which can rise or descend according to its central axis Xa, the movement being transmitted by a motorized system.

Carrying out the photo-oxidation then comprises submission of the coating sample R to exposure to the light of the first lamp 6a. During this exposure, the first chamber 2 is subjected to first accelerated aging test parameters, i.e. a first temperature Ta of between 0 and 250° C., and for example approximately 70° C., and a first level of humidity Rha of between 0 and 100%. These first accelerated aging test parameters are regulated by sensors of the device 1.

In addition, during the rotation of the first support part 7a of the support 7 relative to the second support part 7b which forms a base, in other words during the rotation of the first support part 7a around the first lamp 6a, liquid is sprayed by the first liquid spraying system 5a of the first chamber 2.

At the end of the exposure of the coating sample R to the first lamp 6a, this first lamp 6a automatically rises in order to be accommodated in the first compartment 17a.

Then, the method comprises opening of the mobile partition 4 in order to permit the displacement of the support 7 from the first chamber 2 to the second chamber 3. For this purpose, the second support part 7b is displaced by its notched wheels 8 on the notched rail 9 which extends from the first chamber 2 as far as the second chamber 3.

The method then comprises closure of the mobile partition 4 when the support 7 is situated in the second chamber 3. By this structure, the two chambers 2, 3 are isolated from one another.

It should be noted that, in this example, the mobile partition 4 is opened and closed by vertical displacement of the mobile partition 4. However, as a variant, the mobile partition 4 could be displaced laterally.

It is thus possible to carry out step ii) of the method according to the disclosure herein, which consists of or comprises creating mechanical stresses by thermal shocks.

For this purpose, the step ii) comprises submission of the second chamber 3 to second accelerated aging test parameters, i.e. a second temperature Tb of between −70 and 250° C., and for example approximately −70° C., and a second level of humidity Rhb of between 0 and 100%. These second accelerated aging test parameters are regulated by sensors of the device 1.

As can be seen, the second temperature Tb is distinctly lower than the first temperature Ta, such as to generate mechanical stresses by thermal shocks.

In addition, the coating sample R can also be subjected to exposure to the light of the second lamp 6b of the second chamber 3 which is closed by the mobile partition 4. This second lamp 6b can also be a lamp of the xenon or mercury type. It can be displaced vertically, in order to rise and/or descend, according to its central axis Xb, the movement being transmitted by a motorized system.

Liquid can also be sprayed by a second liquid spraying system 5b which is situated in the second chamber 3.

At the end of the exposure of the coating sample R to the light of the second lamp 6b, the lamp 6b is displaced upwards, in order to be accommodated in the second compartment 17b automatically. The aging cycle is thus finalized and can be repeated a multitude of times in order to reproduce precisely the aging in service. Thus, advantageously, the exposure of the outer coating sample(s) R can be carried out both in the first chamber 2 and in the second chamber 3.

Advantageously, the above-described method according to the disclosure herein can make it possible to reproduce, on at least one outer coating sample R for an aircraft 10, the photo-oxidation of the coating R and the mechanical stresses sustained by the coating R, thanks to the test parameters consisting of or comprising the temperature Ta, Tb and the level of humidity Rha, Rhb, the exposure to the lamps 6a, 6b, the exposure to the liquids of the spraying systems 5a, 5b, and the substantial differences between these parameters, in particular between the two temperatures Ta and Tb, in order to create thermal shocks.

It will be appreciated that the disclosure herein is not limited to the embodiment which has just been described. Various modifications can be made to it by persons skilled in the art.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A device for conducting accelerated aging tests of a coating, the device comprising at least a first test chamber and a second test chamber which are separated by a mobile partition, each chamber being subjected to accelerated aging test parameters, comprising at least temperature and level of humidity, the test parameters being different between the first and second chambers and/or controllable independently between the first and second chambers, each of the first and second chambers additionally comprising a light to generate photo-oxidation, and the device also comprising a support for retention of at least one sample of the coating, the support being displaceable from the first chamber to the second chamber and conversely, after opening of the mobile partition between the first and second chambers in order to generate mechanical stresses by thermal shocks.

2. The device as claimed in claim 1, wherein at least one of the lights is fitted in translation along an axis, so as to be displaceable to and from the at least one sample of the outer coating situated in the support.

3. The device as claimed in claim 1, wherein each light comprises a lamp.

4. The device as claimed in claim 1, comprising a first compartment outside the first chamber and a second compartment outside the second chamber, the first light of the first chamber being able to be accommodated in the first outside compartment in the case when the first light is not used, and the second light of the second chamber being able to be accommodated in the second outside compartment in the case when the second light is not used.

5. The device as claimed in claim 1, wherein the lights are controllable independently from one another.

6. The device as claimed in claim 1, wherein temperature ranges possible in the first and second chambers are different, and selected so as to generate thermal shocks at a passage between the two chambers, the temperature range possible for one of the chambers being between 0 and 250° C., and the temperature range possible for the other one of the chambers being between −70 and 250° C.

7. The device as claimed in claim 1, wherein the range of levels of humidity possible in the first and second chambers is identical for the two chambers.

8. The device as claimed in claim 1, wherein walls of the mobile partition and/or walls of the first and second chambers are thermally insulated in order to permit simultaneous operation of the two chambers at different temperatures.

9. The device as claimed in claim 1, wherein the support comprises a first support part and a second support part, the first support part permitting retention of the at least one sample of the coating, and being fitted such as to rotate relative to the second support part.

10. The device as claimed in claim 9, wherein the second support part comprises elements for displacement of the support, which extend continuously between the first and second chambers.

11. A method for conducting accelerated aging tests of a coating, comprising using a device as claimed in claim 1, and comprising carrying out once or more of step i) of optical stresses by photo-oxidation, and/or a step ii) of mechanical stresses by thermal shocks, as described hereinafter:
   i) submission of at least one sample of the coating, retained by the support situated in the first chamber or in the second chamber, while the mobile partition is closed, to exposure to light of a first light of the first chamber, or respectively of a second light of the second chamber;
   ii) submission of at least one sample of the coating, retained by the support situated in the first chamber or in the second chamber, while the mobile partition is closed, to first accelerated aging test parameters comprising at least a first temperature and a first level of humidity, or respectively to second accelerated aging test parameters comprising at least a second temperature and a second level of humidity; then opening of the mobile partition in order to permit displacement of the support from the first chamber to the second chamber, or respectively from the second chamber to the first chamber, and closure of the mobile partition when the support is situated in the second chamber, or respectively in the first chamber; and submission of the second chamber to second accelerated aging test parameters comprising at least a second temperature and a second level of humidity, or respectively submission of the first chamber to first accelerated aging test parameters comprising at least a first temperature and a first level of humidity, at least the first and second temperatures being different, such as to generate thermal shocks.

12. The method as claimed in claim 11, wherein, in the step ii) of mechanical stresses by thermal shocks, the temperature difference between the first and second temperatures is equal to, or more than, 100° C.

13. The method as claimed in claim 11, comprising the implementation in succession of at least one step i) of optical stresses by photo-oxidation, then at least one step ii) of mechanical stresses by thermal shocks, or conversely.

14. The method as claimed in claim 11, wherein, during at least one step ii) of mechanical stresses by thermal shocks, comprising submission of the at least one sample of the coating, retained by the support situated in the first chamber or in the second chamber, while the mobile partition is closed, to exposure to light of a first light of the first chamber, or respectively of a second light of the second chamber.

15. The method as claimed in claim 11, wherein, during at least one step i) of optical stresses by photo-oxidation, the method comprises spraying of a liquid into the first chamber or into the second chamber by a first liquid spraying system, or respectively by a second liquid spraying system.

16. The method as claimed in claim 15, comprising spraying of a liquid during rotation of a first support part relative to a second support part of the support.

* * * * *